United States Patent [19]

Barreau et al.

[11] 4,144,339
[45] Mar. 13, 1979

[54] 1,2-DITHIOLE PYRIMIDINES

[75] Inventors: Michel Barreau; Claude Cotrel, both of Paris; Claude Jeanmart, Brunoy, all of France

[73] Assignee: Rhone-Poulenc Industries, Paris, France

[21] Appl. No.: 855,196

[22] Filed: Nov. 28, 1977

Related U.S. Application Data

[62] Division of Ser. No. 766,966, Feb. 9, 1977, Pat. No. 4,110,450.

[30] Foreign Application Priority Data

Feb. 10, 1976 [FR] France ............................. 76 03604
Dec. 23, 1976 [FR] France ............................. 76 38901

[51] Int. Cl.² .......................................... A61K 31/505
[52] U.S. Cl. .............................. 424/251; 260/326.82; 544/122; 544/333; 544/336
[58] Field of Search ................ 260/256.5 R, 256.4 R; 544/122, 333; 424/251

[56] References Cited

U.S. PATENT DOCUMENTS 3,979,388  9/1976  Krenzer ...................... 260/256.5 R

FOREIGN PATENT DOCUMENTS 1526768 11/1963 France.

OTHER PUBLICATIONS

"The Chemistry of Heterocyclic Compounds", vol. 21, First Part, pp. 382-384 (1966).
Bottcher et al., Chem. Ber. 84, pp. 458-463 (1951).
Legrand et al., Bull. Soc. Chim, France, pp. 79-83 (1955).

Primary Examiner—Jose Tovar
Assistant Examiner—Lisa Jones
Attorney, Agent, or Firm—Stevens, Davis, Miller & Mosher

[57] ABSTRACT 1,2-Dithiole derivatives of the formula:

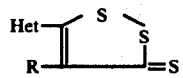

wherein Het represents an aromatic heterocyclic radical with six atoms in the ring two of which are nitrogen atoms, the heterocyclic radical optionally carrying a single substituent selected from halogen, alkyl, alkoxy, mercapto, alkylthio, dialkylamino, pyrrolidin-1-yl, piperidino, morpholino and 4-alkylpiperazin-1-yl, and R represents halogen, alkyl (optionally substituted by alkoxycarbonyl), carboxy, alkoxycarbonyl, carbamoyl, N-alkylcarbamoyl or a group $R_1$—CH(OH)— in which $R_1$ represents hydrogen or alkyl, the said alkyl, alkoxy and alkylthio radicals or alkyl or alkoxy moieties containing 1 to 4 carbon atoms except in the case of $R_1$ which contains 1 to 3 carbon atoms when an alkyl radical, are new compounds useful in the treatment of bilharziasis.

7 Claims, No Drawings

1,2-DITHIOLE PYRIMIDINES

This is a division of application Ser. No. 766,966 filed Feb. 9, 1977, now U.S. Pat. No. 4,110,450.

This invention relates to new therapeutically useful derivatives of 1,2-dithiole, to processes for their preparation and pharmaceutical compositions containing them.

The new derivatives of 1,2-dithiole of the present invention are those compounds of the general formula:

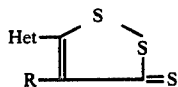    I wherein Het represents an aromatic heterocyclic radical with six atoms in the ring two of which are nitrogen atoms (viz. a pyridazin-3-yl or -4-yl radical, a pyrimidin-2-yl, -4-yl or -5-yl radical, or pyrazin-2-yl radical), optionally substituted by a halogen atom or by an alkyl radical containing 1 to 4 carbon atoms, an alkoxy radical containing 1 to 4 carbon atoms, a mercapto radical, an alkylthio radical containing 1 to 4 carbon atoms, a dialkylamino group of which each alkyl radical contains 1 to 4 carbon atoms, a pyrrolidin-1-yl, piperidino or morpholino radical, or a 4-alkylpiperazin-1-yl group of which the alkyl radical contains 1 to 4 carbon atoms, and R represents a halogen atom or an alkyl radical containing 1 to 4 carbon atoms (optionally substituted by an alkoxycarbonyl group containing 1 to 4 carbon atoms in the alkoxy radical), a carboxy radical, an alkoxycarbonyl group containing 1 to 4 carbon atoms in the alkoxy radical, a carbamoyl radical, an N-alkylcarbamoyl group in which the alkyl radical contains 1 to 4 carbon atoms, or a group $R_1$—CH(OH)— in which $R_1$ represents a hydrogen atom or an alkyl radical containing 1 to 3 carbon atoms.

According to a feature of the invention, the compounds of general formula I, wherein Het is as hereinbefore defined and R represents a halogen atom or an alkyl radical containing 1 to 4 carbon atoms (optionally substituted by an alkoxycarbonyl group containing 1 to 4 carbon atoms in the alkoxy radical) or an alkoxycarbonyl group containing 1 to 4 carbon atoms in the alkoxy radical, are prepared by the process which comprises reacting phosphorus pentasulphide with a heterocyclic compound of the general formula:

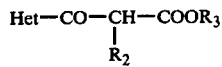    II wherein Het is as hereinbefore defined, $R_2$ represents a halogen atom or an alkyl radical containing 1 to 4 carbon atoms (optionally substituted by an alkoxycarbonyl group containing 1 to 4 carbon atoms in the alkoxy radical) or an alkoxycarbonyl group containing 1 to 4 carbon atoms in the alkoxy radical and $R_3$ represents an alkyl radical containing 1 to 4 carbon atoms.

The reaction is generally carried out in an organic solvent which is inert towards phosphorus pentasulphide, such as pyridine, benzene, toluene, xylene or chlorobenzene, at a temperature between 50° and 200° C.

During the course of the reaction of phosphorus pentasulphide with a compound of general formula II wherein the heterocyclic radical Het carries on a carbon atom in α-position to a nitrogen atom an alkoxy radical containing 1 to 4 carbon atoms, there is formed, alongside a compound of general formula I wherein Het is a heterocyclic radical as hereinbefore defined substituted in α-position to a nitrogen atom by an alkoxy radical containing 1 to 4 carbon atoms, a compound of general formula I wherein Het is a heterocyclic radical as hereinbefore defined substituted in α-position to a nitrogen atom by a mercapto radical.

The heterocyclic compounds of general formula II, wherein $R_2$ represents a halogen atom, preferably a chlorine or bromine atom, and Het and $R_3$ are as hereinbefore defined, can be obtained by the action of a halogenating agent on a β-keto-ester of the general formula:

$$\text{Het} - \text{CO} - \text{CH}_2 - \text{COOR}_3 \qquad \text{III}$$

wherein Het and $R_3$ are as hereinbefore defined. Preferably a sulphuryl halide is used as the halogenating agent, and the reaction is carried out in an inert organic solvent such as methylene chloride at a temperature between 30° and 50° C.

The heterocyclic compounds of general formula II, wherein $R_2$ represents an alkyl radical containing 1 to 4 carbon atoms (optionally substituted by an alkoxycarbonyl group containing 1 to 4 carbon atoms in the alkoxy radical) or an alkoxycarbonyl group containing 1 to 4 carbon atoms in the alkoxy radical, can be obtained according to one of the following methods: (a) by reacting an ester of the general formula:

$$R_4 - \text{CH}_2 - \text{COOR}_3 \qquad \text{IV}$$

(wherein $R_4$ represents an alkyl radical containing 1 to 4 carbon atoms (optionally substituted by an alkoxycarbonyl group containing 1 to 4 carbon atoms in the alkoxy radical) or an alkoxycarbonyl group containing 1 to 4 carbon atoms in the alkoxy radical, and $R_3$ is as hereinbefore defined) with a heterocyclic derivative of the general formula:

$$\text{Het} - \text{COOR}_5 \qquad \text{V}$$

wherein Het is as hereinbefore defined and $R_5$ represents an alkyl radical containing 1 to 4 carbon atoms.

The reaction is generally carried out under the usual conditions for the Claisen reaction for the preparation of β-keto-esters. More particularly, the condensation can be effected at a temperature between 10° and 100° C. in the presence of an alkoxide, such as sodium ethoxide or sodium tert.-butoxide, optionally working in an anhydrous organic solvent such as an aromatic hydrocarbon (e.g. benzene, toluene or xylene) and removing, by distillation, the alcohol $R_5$—OH ($R_5$ being as hereinbefore defined) formed during the reaction.

It is also possible to effect the condensation in the presence of sodium hydride in diethyl ether. (b) by reacting a reactive ester of the general formula:

$$R_4 - Z \qquad \text{VI}$$

(wherein $R_4$ is as defined above, and Z represents the acid residue of a reactive ester such as a halogen atom or a sulphuric or sulphonic ester radical) with a β-keto-ester of general formula III.

The reaction is generally carried out in an organic solvent such as acetone in the presence of a condensation agent such as an alkali metal carbonate, for example sodium or potassium carbonate, and optionally in the presence of an alkali metal iodide such as sodium or potassium iodide, or in an organic solvent such as an ether or an aromatic hydrocarbon in the presence of sodium ethoxide or sodium hydride.

The β-keto-esters of general formula III can be obtained by the action of an acetic acid ester of the general formula:

$$CH_3 - COOR_3 \quad \text{VII}$$

(wherein $R_3$ is as defined above) on a heterocyclic compound of general formula V under the conditions mentioned above for the reaction between an ester of general formula IV and a heterocyclic compound of general formula V.

The heterocyclic compounds of general formula II, wherein $R_2$ represents an alkoxycarbonyl group containing 1 to 4 carbon atoms in the alkoxy radical, and Het and $R_3$ are as hereinbefore defined, can also be obtained by the action of an acid halide of the general formula:

$$Het - CO - Cl \quad \text{VIII}$$

(wherein Het is as hereinbefore defined), or of a mixed anhydride of the general formula:

$$Het - CO - O - CO - OR_6 \quad \text{IX}$$

(wherein Het is as hereinbefore defined and $R_6$ represents an alkyl radical containing 1 to 4 carbon atoms), on a magnesium derivative of a malonic ester of the general formula:

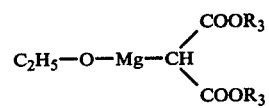
$$\text{X}$$

wherein $R_3$ is as hereinbefore defined and is identical to the alkyl moiety of the alkoxycarbonyl group of the radical $R_2$ mentioned above.

Generally the reaction is carried out in an anhydrous organic solvent such as diethyl ether, operating at a temperature between 0° C. and the boiling point of the reaction mixture.

The mixed anhydrides of general formula IX can be obtained by the action of an alkyl chloroformate, the said alkyl radical containing 1 to 4 carbon atoms, on an acid of the general formula:

$$Het - COOH \quad \text{XI}$$

wherein Het is as hereinbefore defined.

According to another feature of the invention, the compounds of general formula I wherein R represents the carboxy radical, that is to say the acid compounds of the general formula:

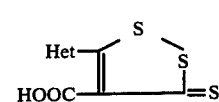
$$\text{XII}$$

(wherein Het is as hereinbefore defined) are prepared by the process which comprises the hydrolysis of a compound of general formula I wherein R represents an alkoxycarbonyl radical, that is to say a compound of the general formula:

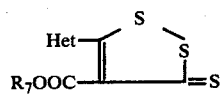
$$\text{XIII}$$

(wherein $R_7$ represents an alkyl radical containing 1 to 4 carbon atoms and Het is as hereinbefore defined), by methods known per se for the hydrolysis of an alkoxycarbonyl group to a carboxy radical without affecting the rest of the molecule. By the term "methods known per se" as used in this specification is meant methods heretofore used or described in the chemical literature.

Generally, the hydrolysis is effected in an acid medium at the boiling point of the reaction mixture. Preferably an inorganic acid, such as sulphuric acid, is used in an aqueous organic medium.

According to a still further feature of the invention, the compounds of general formula I wherein R represents a carbamoyl or an N-alkylcarbamoyl radical, that is to say the compounds of the general formula:

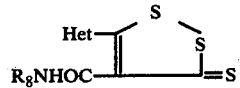
$$\text{XIV}$$

(wherein Het is as hereinbefore defined and $R_8$ represents a hydrogen atom or an alkyl radical containing 1 to 4 carbon atoms), are prepared by the action of ammonia or of an amine of the general formula:

$$H_2N - R_9 \quad \text{XV}$$

(wherein $R_9$ represents an alkyl radical containing 1 to 4 carbon atoms) on an acid of general formula XII.

It is particularly advantageous to activate initially the carboxy radical by reacting the acid of general formula XII with an alkyl chloroformate or with 1-ethoxycarbonyl-2-ethoxy-1,2-dihydroquinoline, operating in an inert organic solvent such as methylene chloride or dimethylformamide, and then, in situ, reacting the intermediate product obtained with ammonia or with an amine of general formula XV, optionally in solution in an organic solvent such as methanol.

According to another feature of the invention, the compounds of general formula I, wherein R represents an alkoxycarbonyl group containing 1 to 4 carbon atoms in the alkoxy radical are prepared by the esterification of an acid of general formula XII by methods known per se.

Generally an excess of the corresponding alcohol containing 1 to 4 carbon atoms is reacted with the acid of the general formula XII, in the presence of a strong acid such as sulphuric acid, methanesulphonic acid or p-toluenesulphonic acid, operating at the boiling point of the reaction mixture.

Esterification of an acid of general formula XII can also be carried out by reacting an alkali metal salt, an amine salt or a quaternary ammonium salt, of the acid with a reactive ester of the general formula:

$$X - R_7 \quad \text{XVI}$$

wherein X represents a halogen atom or a sulphuric or sulphonic ester radical, and $R_7$ is as hereinbefore defined.

Generally, the reaction is carried out in an inert organic solvent, such as methylene chloride, hexamethylphosphotriamide or dimethylformamide, at a temperature between 0° and 60° C.

According to another feature of the invention, the compounds of general formula I, wherein Het is as hereinbefore defined and R represents a group $R_1$—CH(OH)— ($R_1$ being as hereinbefore defined), are prepared by the action of phosphorus pentasulphide on a 1,2-dithiol-3-one of the general formula:

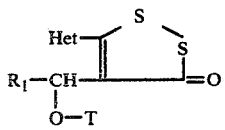

XVII wherein Het is as hereinbefore defined and T represents a protective group for the alcohol function, followed by the replacement of the radical T by a hydrogen atom by hydrolysis in an acid medium. Preferably a dialkoxyacetyl group (of which each alkoxy radical contains 1 to 3 carbon atoms), or a formyl, acetyl or trifluoroacetyl radical, is used to protect the alcohol function.

Generally, the phosphorus pentasulphide is reacted with a compound of general formula XVII suspended in an organic solvent which is inert to phosphorus pentasulphide, such as dioxan, pyridine, benzene, toluene, xylene or chlorobenzene, at a temperature between 50° C. and 200° C.

The replacement of the protective group by a hydrogen atom generally takes place by heating the intermediate product in an acid aqueous-organic medium. Preferably the hydrolysis is effected in an organic solvent such as acetone in the presence of sulphuric or hydrochloric acid in aqueous solution.

The 1,2-dithiole-3-ones of general formula XVII can be obtained by the action of an alkali metal salt of a carboxylic acid such as formic, acetic or trifluoroacetic acid or a dialkoxyacetic acid (of which each alkoxy radical contains 1 to 3 carbon atoms) on a 1,2-dithiole-3-one of the general formula:

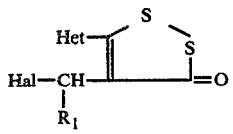

XVIII wherein Het and $R_1$ are as hereinbefore defined, and Hal represents a halogen atom, preferably a bromine or chlorine atom.

Generally, the reaction is carried out by heating the reactants in an organic solvent such as acetone.

The compounds of general formula XVIII can be obtained by the action of a suitable halogenating agent on a compound of the general formula:

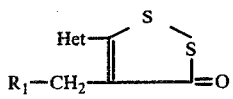

XIX wherein Het and $R_1$ are as hereinbefore defined. Preferably N-bromosuccinimide is used as the halogenating agent, operating in an organic solvent such as carbon tetrachloride and in the presence of an initiator of free radical reactions such as azobisisobutyronitrile.

The compounds of general formula XIX can be obtained by the action of mercuric acetate on a compound of general formula I, wherein Het is as hereinbefore defined and R represents an alkyl radical containing 1 to 4 carbon atoms. Generally the reaction is effected at a temperature between 50° and 120° C. in an organic solvent, such as an acid, e.g. acetic acid.

The new compounds of general formula I obtained by the aforedescribed processes can be purified, if desired, by physical methods such as crystallisation or chromatography.

The 1,2-dithiole derivatives of general formula I exhibit remarkable chemotherapeutic properties. They are particularly useful as anti-bilharzia agents. Furthermore, they have a low toxicity and, for the great majority of the compounds, the 50% lethal dose ($LD_{50}$) is greater than 1000 mg/kg animal body weight when administered orally to mice.

The anti-bilharzia activity manifests itself in mice infested with *Schistosome mansoni* at doses of between 10 and 1000 mg/kg animal body weight per day when administered orally or subcutaneously for 5 days. After a single treatment, this activity manifests itself at doses of between 100 and 500 mg/kg animal body weight when administered orally or subcutaneously.

In monkeys [*Maccaca mulatta* (var. rhesus)] the anti-bilharzia activity manifests itself at doses of between 5 and 100 mg/kg animal body weight per day when administered orally for 5 days.

Of very particular interest are the compounds of general formula I wherein Het represents a pyridazin-3-yl or -4-yl radical, a pyrimidin-2-yl, -4-yl or -5-yl radical or a pyrazin-2-yl radical, optionally substituted by a halogen atom or by an alkyl radical containing 1 to 4 carbon atoms, an alkylthio radical containing 1 to 4 carbon atoms, a dialkylamino group of which each alkyl radical contains 1 to 4 carbon atoms, a pyrrolidin-1-yl or piperidino radical or a 4-alkylpiperazin-1-yl group of which the alkyl radical contains 1 to 4 carbon atoms, and R represents an alkyl radical containing 1 to 4 carbon atoms, an alkoxycarbonyl group containing 1 to 4 carbon atoms or a group $R_1$—CH(OH)— in which $R_1$ represents an alkyl radical containing 1 to 3 carbon atoms or preferably a hydrogen atom.

Of such compounds those of outstanding interest are 4-methyl-5-(pyrazin-2-yl)-1,2-dithiole-3-thione, 4-ethyl-5-(pyrazin-2-yl)-1,2-dithiole-3-thione, 4-methyl-5-(pyridazin-3-yl)-1,2-dithiole-3-thione, 4-ethyl-5-(pyridazin-3-yl)-1,2-dithiole-3-thione, 4-methyl-5-(pyridazin-4-yl)-1,2-dithiole-3-thione, 4-butyl-5-(pyridazin-3-yl)-1,2-dithiole-3-thione, 4-methyl-5-(5-methylpyrazin-2-yl)-1,2-dithiole-3-thione, 4-ethyl-5-(pyrimidin-5-yl)-1,2-dithiole-3-thione, 4-methyl-5-(5-methylthiopyrimidin-4-yl)-1,2-dithiole-3-thione, 5-(6-dimethylaminopyridazin-3-yl)-4-methyl-1,2-dithiole-3-thione and 5-(5-chloropyrimidin-4-yl)-4-methyl-1,2-dithiole-3-thione.

The following non-limitative Examples illustrate the preparation of 1,2-dithiole derivatives of the present invention.

EXAMPLE 1

A suspension of ethyl 2-butyl-3-(pyrazin-2-yl)-3-oxopropionate (54.7 g) and phosphorus pentasulphide (53.4 g) in toluene (550 cc) is heated for one hour at a temperature of about 110° C. After cooling to a temperature of about 20° C., methylene chloride (600 cc) and a saturated aqueous sodium bicarbonate solution (600 cc) are added to the suspension obtained, and the mixture is stirred for 12 hours at a temperature of about 20° C. The suspension is then filtered and the aqueous phase is decanted and washed with methylene chloride (500 cc). The combined organic phases are washed with water (2 × 300 cc), dried over magnesium sulphate in the presence of decolourizing charcoal, filtered and evaporated to dryness under reduced pressure. The residue obtained is then dissolved in methylene chloride (50 cc) and the resulting solution is filtered over silica gel (780 g) contained in a column 6 cm in diameter. The column is eluted with pure methylene chloride (1000 cc). This eluate is discarded. The column is then eluted with pure methylene chloride (2500 cc). The resulting eluate is evaporated to dryness under reduced pressure (20 mm Hg). 4-Butyl-5-(pyrazin-2-yl)-1,2-dithiole-3-thione (3.1 g), melting at 72° C., is obtained after recrystallisation of the residue obtained from acetonitrile (40 cc).

Ethyl 2-butyl-3-(pyrazin-2-yl)-3-oxopropionate can be prepared by heating a suspension of ethyl 3-(pyrazin-2-yl)-3-oxopropionate (58.8 g), iodobutane (67.8 g) and dry potassium carbonate (38.7 g), in acetone (400 cc) for 20 hours at a temperature of about 60° C. After cooling to a temperature of about 20° C., the reaction mixture is filtered and the insoluble product is washed with acetone (3 × 50 cc). The filtrate is evaporated to dryness under reduced pressure. The residue obtained is taken up in methylene chloride (450 cc) and the solution obtained is dried over anhydrous magnesium sulphate in the presence of decolourizing charcoal, filtered and evaporated to dryness under reduced pressure (20 mm Hg). Ethyl 2-butyl-3-(pyrazin-2-yl)-3-oxopropionate (54.7 g) is thus obtained in the form of a yellow oil.

EXAMPLE 2

By proceeding as in Example 1 but starting with ethyl 2-methyl-3-(pyrazin-2-yl)-3-oxopropionate (41.2 g) and phosphorus pentasulphide (42.4 g) suspended in toluene (410 cc), 4-methyl-5-(pyrazin-2-yl)-1,2-dithiole-3-thione (3.42 g), melting at 164° C., is obtained after recrystallisation of the residue from 1,2-dichloroethane (30 cc).

Ethyl 2-methyl-3-(pyrazin-2-yl)-3-oxopropionate can be prepared from ethyl 3-(pyrazin-2-yl)-3-oxopropionate (38.8 g), methyl iodide (34.8 g) and dry potassium carbonate (25.8 g) suspended in acetone (50 cc). Ethyl 2-methyl-3-(pyrazin-2-yl)-3-oxopropionate (41.2 g) is obtained in the form of a yellow oil.

EXAMPLE 3

Proceeding as in Example 1 but starting with ethyl 2-ethyl-3-(pyrazin-2-yl)-3-oxopropionate (187.2 g) and phosphorus pentasulphide (210.9 g) suspended in toluene (1,870 cc), 4-ethyl-5-(pyrazin-2-yl)-1,2-dithiole-3-thione (5.7 g), melting at 121° C., is obtained after recrystallisation of the residue from acetonitrile (80 cc).

Ethyl 2-ethyl-3-(pyrazin-2-yl)-3-oxopropionate can be prepared from ethyl 3-(pyrazin-2-yl)-3-oxopropionate (155.2 g), ethyl iodide (153.6 g) and dry potassium carbonate (103.2 g), suspended in acetone (400 cc). Ethyl 2-ethyl-3-(pyrazin-2-yl)-3-oxopropionate (180 g) is obtained in the form of a brown oil.

EXAMPLE 4

A suspension of ethyl 2-propyl-3-(pyrazin-2-yl)-3-oxopropionate (128.5 g) and phosphorus pentasulphide (133 g) in pyridine (1000 cc) is heated for one hour at a temperature of about 115° C. After cooling to a temperature of about 60° C., the reaction mixture is poured into distilled water (10,000 cc) and the mixture is allowed to stand for 48 hours at a temperature of about 20° C. The resulting insoluble product is filtered off and washed with methylene chloride (3 × 500 cc). The combined organic phases are dried over magnesium sulphate, filtered and evaporated to dryness under reduced pressure. The residue obtained is dissolved in methylene chloride (250 cc) and the resulting solution is filtered over silica gel (1600 g) contained in a column 7 cm in diameter. The column is eluted with pure methylene chloride (6000 cc). This eluate is discarded. Thereafter the column is eluted with pure methylene chloride (4000 cc). The eluate obtained is evaporated to dryness under reduced pressure. After recrystallisation of the residue from acetonitrile (193 cc), 4-propyl-5-(pyrazin-2-yl)-1,2-dithiole-3-thione (11 g), melting at 125° C., is obtained.

Ethyl 2-propyl-3-(pyrazin-2-yl)-3-oxopropionate can be prepared from ethyl 3-(pyrazin-2-yl)-3-oxopropionate (145.5 g), propyl bromide (113.5 g), potassium iodide (124.5 g) and dry potassium carbonate (95.2 g), suspended in acetone (1000 cc). Ethyl 2-propyl-3-(pyrazin-2-yl)-3-oxopropionate (148 g) is obtained, after purification, in the form of a brown oil.

EXAMPLE 5

Proceeding as in Example 4 but starting with ethyl 2-methyl-3-(5-methylpyrazin-2-yl)-3-oxopropionate (11.1 g) and phosphorus pentasulphide (12.2 g) suspended in pyridine (120 cc), 4-methyl-5-(5-methylpyrazin-2-yl)-1,2-dithiole-3-thione (1.1 g), melting at 162°–163° C., is obtained after recrystallisation of the residue from acetonitrile (70 cc).

Ethyl 2-methyl-3-(5-methylpyrazin-2-yl)-3-oxopropionate can be prepared from ethyl 3-(5-methylpyrazin-2-yl)-3-oxopropionate (12.6g), methyl iodide (10.6 g) and dry potassium carbonate (7.6 g) suspended in acetone (80 cc). Ethyl 2-methyl-3-(5-methylpyrazin-2-yl)-3-oxopropionate (11.4 g) is obtained in the form of an orange oil.

Ethyl 3-(5-methylpyrazin-2-yl)-3-oxopropionate can be prepared by the action of ethyl acetate on 5-methyl-2-ethoxycarbonylpyrazine in toluene in the presence of sodium ethoxide at a temperature of about 80° C. for 4 hours.

5-Methyl-2-ethoxycarbonylpyrazine can be prepared by the action of excess ethanol on 5-methyl-2-carboxypyrazine under reflux for 13 hours, in the presence of concentrated sulphuric acid.

5-Methyl-2-carboxypyrazine can be prepared according to the method described by W. Schwaiger et al., Rec. Trav. Chim. Pays-Bas, 91, 1175 (1972).

EXAMPLE 6

A suspension of ethyl 2-ethyl-3-[6-(4-methylpiperazin-1-yl)pyridazin-3-yl]-3-oxopropionate (3.8 g) and phosphorus pentasulphide (7.9 g) in pyridine (50 cc) is heated for 1 hour at a temperature of about 115° C. After cooling to a temperature of about 20° C., the reaction mixture is poured into distilled water (500 cc), and the mixture is allowed to stand for 5 hours at a temperature of about 20° C. The resulting insoluble product is filtered off and washed with distilled water (2 × 30 cc). The product thus obtained is stirred for 20 minutes at a temperature of about 20° C. with chloroform (100 cc), 11N ammonia (35 cc) and distilled water (15 cc). The aqueous phase is then decanted and washed with chloroform (25 cc). The combined organic phases are dried over magnesium sulphate, filtered and evaporated to dryness under reduced pressure. The residue obtained is stirred for 10 minutes at a temperature of about 20° C. in diethyl ether (50 cc) and then the insoluble material is filtered off and washed with diethyl ether (4 × 25 cc). The filtrates are combined and evaporated to dryness under reduced pressure. The residue obtained is dissolved in methylene chloride (10 cc) and filtered over silica gel (6 g) contained in a column 1 cm in diameter. The column is eluted, firstly, with a mixture (600 cc) of methylene chloride and methanol (99:1 by volume). This eluate is discarded. Thereafter the column is eluted with a mixture (100 cc) of methylene chloride and methanol (99:1 by volume). The corresponding eluate is evaporated to dryness under reduced pressure. 4-Ethyl-5-[6-(4-methylpiperazin-1-yl)pyridazin-3-yl]-1,2-dithiole-b 3-thione (0.06 g), melting at 182° C., is obtained.

Ethyl 2-ethyl-3-[6-(4-methylpiperazin-1-yl)pyridazin-3-yl]-3-oxopropionate can be prepared from ethyl [6-(4-methylpiperazin-1-yl)pyridazin-3-yl]-carboxylate (8 g), ethyl butyrate (4.4 g) and sodium tert.-butoxide (3.65 g) suspended in dry toluene (120 cc). Ethyl 2-ethyl-3-[6-(4-methylpiperazin-1-yl)pyridazin-3-yl]-3-oxopropionate (6.1 g), is thus obtained in the form of a brown oil.

Ethyl [6-(4-methylpiperazin-1-yl)pyridazin-3-yl]-carboxylate can be obtained by heating a suspension of 3-cyano-6-(4-methylpiperazin-1-yl)pyridazine (40.7 g ) in a mixture of distilled water (300 cc), ethanol (200 cc) and 10N aqueous sodium hydroxide (100 cc) at a temperature of about 80° C. for 5 hours. After cooling to a temperature of about 20° C., methylene chloride (200 cc) is added to the reaction mixture and the aqueous phase is decanted, acidified with 12N hydrochloric acid (100 cc) and evaporated to dryness under reduced pressure. Ethanol (250 cc), 1,2-dichloroethane (250 cc) and pure methanesulphonic acid (52.5 g) are added to the residue obtained. The resulting mixure is then heated under reflux for 20 hours. After cooling to a temperature of about 20° C., the insoluble material is filtered off and washed with methylene chloride (2 × 100 cc). A saturated aqueous solution of sodium carbonate (1000 cc) is added to the filtrate thus obtained. The resulting insoluble product is filtered off and washed with methylene chloride (2 × 200 cc). The aqueous phase is decanted and washed with methylene chloride (2 × 200 cc). The organic fractions are combined, dried over magnesium sulphate, filtered and evaporated to dryness under reduced pressure. Ethyl [6-(4-methylpiperazin-1-yl)pyridazin-3-yl]-carboxylate (9.5 g), melting at 106° C., is obtained. 3-Cyano-6-(4-methylpiperazin-1-yl)pyridazine can be prepared from 6-(4-methylpiperazin-1-yl)-3-iodopyridazine (125 g) and cuprous cyanide (55.26 g) suspended in dimethylformamide (620 cc). 3-Cyano-6-(4-methylpiperazin-1-yl)pyridazine (52.1 g), melting at 149° C., is obtained.

3-Iodo-6-(4-methylpiperazin-1-yl)pyridazine can be obtained from 3,6-diiodopyridazine (158.5 g) and 4-methylpiperazine (120 g) suspended in methanol (1200 cc). 3-Iodo-6-(4-methylpiperazin-1-yl)pyridazine (138.7 g), melting at 149° C., is obtained.

EXAMPLE 7

A solution of ethyl 2-methyl-3-(pyridazine3-yl)-3-oxopropionate (113.8 g) in toluene (500 cc) is added over a period of 25 minutes to a suspension of phosphorus pentasulphide (182 g) in toluene (1300 cc), heated under reflux. The heating under reflux is continued for 1 hour after the end of the addition. After cooling to a temperature of about 20° C., the resulting insoluble product is filtered off, and subsequently stirred for 45 minutes at a temperature of about 20° C. with a mixture of chloroform (1500 cc), distilled water (500 cc) and 11N ammonia (1000 cc). After filtration of the insoluble residue, the organic phase is decanted, dried over magnesium sulphate, filtered and evaporated to dryness under reduced pressure. The residue obtained is washed with diethyl ether (500 cc) and then with methylene chloride (250 cc). 4-Methyl-5-(pyridazin-3yl)-1,2-dithiole-3-thione (4.86 g), melting at 193° C., is obtained after recrystallisation of the residue from 1,2-dichloroethane (380 cc).

Ethyl 2-methyl-3-(pyridazin-3yl)-3-oxopropionate can be prepared by adding a solution of ethyl (pyridazin-3-yl)-carboxylate (304 g) and ethyl propionate (204 g) in anhydrous toluene (1000 cc), over a period of 13 minutes at a temperature of about 35° C., to a suspension of sodium tert.-butoxide (192 g) in anhydrous toluene (3000 cc). The reaction mixture is stirred for 12 hours at a temperature of about 20° C. and then distilled water (3000 cc) is added. The aqueous phase is decanted and, after acidification with 12N hydrochloric acid (150 cc), it is washed by decantation with methylene chloride (1500 cc) and then with methylene chloride (3 × 500 cc). The combined organic phases are dried over magnesium sulphate, filtered and evaporated to dryness under reduced pressure. Ethyl 2-methyl-3-(pyridazin-3-yl)-3-oxopropionate (227.7 g) is thus obtained in the form of a red oil.

Ethyl (pyridazin-3-yl)-carboxylate can be prepared in accordance with the method described by W. J. Laenza et al., J. Amer. Chem. Soc. 75, 4086 (1953).

EXAMPLE 8

Proceeding as in Example 7 but starting with ethyl 2-(pyridazin-3-yl)carbonylhexanoate (80 g) and phosphorus pentasulphide (106.5 g) suspended in toluene (1200 cc), 4-butyl-5-(pyridazin-3-yl)-1,2-dithiole-3-thione (4 g), melting at 94° C., is obtained after recrystallisation of the residue from ethyl acetate (10 cc).

Ethyl 2-(pyridazin-3-yl)carbonylhexanoate can be prepared from ethyl (pyridazin-3-yl)-carboxylate (114 g), ethyl hexanoate (108 g) and sodium tert.-butoxide (72 g), suspended in anhydrous toluene (1500 cc). Ethyl 2-(pyridazin-3-yl)carbonylhexanoate (160 g) is obtained in the form of a brown oil.

EXAMPLE 9

Proceeding as in Example 7 but starting with ethyl 2-methyl-3-(pyridazin-4-yl)-3-oxopropionate (206 g) and phosphorus pentasulphide (220 g) suspended in toluene (2060 cc), 4-methyl-5-(pyridazin-4-yl)-1,2-dithiole-3-thione (5.15 g), melting at 146° C. and then 150° C., is obtained after recrystallisation of the residue from acetonitrile (120 cc).

Ethyl 2-methyl-3-(pyridazin-4-yl)-3-oxopropionate can be prepared from ethyl (pyridazin-4-yl)-carboxylate (194 g), ethyl propionate (130.5 g) and sodium tert.-butoxide (123 g) suspended in anhydrous toluene (3240 cc). Ethyl 2-methyl-3-(pyridazin-4-yl)-3-oxopropionate (206 g) is obtained in the form of a brown oil.

Ethyl (pyridazin-4-yl)-carboxylate can be prepared in accordance with the method described by G. Heinish, Monatsch. Chem. 1973, 104, 953.

EXAMPLE 10

Proceeding as in Example 7 but starting with ethyl 3-(6-methylpyridazin-3-yl)-2-methyl-3-oxoproprionate (1.7 g) and phosphorus pentasulphide (2.55 g) suspended in toluene (34 cc), 5-(6-methylpyridazin-3-yl)-4-methyl-1,2-dithiole-3-thione (0.08 g), melting at 168° C., is obtained after washing the residue with diethyl ether (3 cc).

Ethyl 3-(6-methylpyridazin-3-yl)-2-methyl-3-oxopropionate can be prepared from ethyl (6-methylpyridazin-3-yl)-carboxylate (4.9 g), ethyl propionate (10.5 g) and sodium tert.-butoxide (3.12 g) suspended in tert.-butanol (49 cc). Ethyl 3-(6-methylpyridazin-3-yl)-2-methyl-3-oxopropionate (0.6 g) is obtained in the form of a yellow oil.

Ethyl (6-methylpyridazin-3-yl)-carboxylate can be prepared by heating a suspension of (6-methylpyridazin-3-yl)-carboxylic acid (13.8 g) in ethanol (50 cc), 1,2-dichloroethane (50 cc) and pure methanesulphonic acid (10.6 g) under reflux for 17 hours. After cooling to a temperature of about 20° C., a 10% (w/v) aqueous sodium carbonate solution (100 cc) is added to the reaction mixture. The aqueous phase is decanted and washed with methylene chloride (3 × 70 cc). The combined organic fractions are washed by decantation with distilled water (30 cc) and dried over sodium sulfate. After filtration and concentration to dryness under reduced pressure, ethyl (6-methylpyridazin-3-yl)-carboxylate (14 g) is obtained in the form of a yellow oil.

(6-Methylpyridazin-3-yl)-carboxylic acid can be prepared by heating a solution of 3-cyano-6-methylpyridazine (68.9 g) in a mixture of distilled water (865 cc), 10N sodium hydroxide solution (290 cc) and ethanol (580 cc) under reflux for one hour. After cooling to a temperature of about 20° C., 12N hydrochloric acid (250 cc) is added to the reaction mixture. After concentration to dryness under reduced pressure, ethanol (1400 cc) is added to the residue obtained and the suspension is stirred for 70 minutes at a temperature of about 20° C. The insoluble product is then filtered off and washed with ethanol (3 × 100 cc). The combined filtrates are evaporated to dryness under reduced pressure. (6-Methylpyridazin-3-yl)-carboxylic acid (70 g), melting at 174° C. with decomposition, is obtained.

3-Cyano-6-methylpyridazine can be prepared in accordance with the method described by Masaru Ogata, Chem. Pharm. Bull. 11, 1511 (1963).

EXAMPLE 11

A suspension of ethyl 2-ethyl-3-(pyridazin-3-yl)-3-oxopropionate (193 g) and phosphorus pentasulphide (231 g) in toluene (3000 cc) is stirred for 15 minutes at a temperature of about 20° C. The reaction mixture is then heated under reflux for one hour. After cooling to a temperature of about 20° C., the insoluble product is filtered off and stirred for one and a half hours with a mixture of chloroform (3000 cc), distilled water (1000 cc) and 11N ammonia (1000 cc). Thereafter the aqueous phase is decanted and washed with chloroform (500 cc). The combined organic fractions are dried over magnesium sulphate, filtered and evaporated to dryness under reduced pressure. The residue obtained is dissolved in methylene chloride (250 cc) and filtered over silica gel (1600 g) contained in a column 6.8 cm in diameter. Thereafter the column is eluted with pure methylene chloride (7000 cc), and then with a mixture (7000 cc) of methylene chloride and methanol (99.5:0.5 by volume). These eluates are discarded. Finally the column is eluted with a mixture (7000 cc) of methylene chloride and methanol (99:1 by volume). The corresponding eluate is evaporated to dryness under reduced pressure, and the residue thus obtained is washed successively with diethyl ether (200 cc), and then with diisopropyl ether (3 × 30 cc). 4-Ethyl-5-(pyridazin-3-yl)-1,2-dithiole-3-thione (7 g), melting at 130° C., is obtained after recrystallisation from methanol (500 cc).

Ethyl 2-ethyl-3-(pyridazin-3-yl)-3-oxopropionate can be prepared from ethyl (pyridazin-3-yl)-carboxylate (201.7 g), ethyl butyrate (153.9 g) and sodium tert.-butoxide (127.2 g) suspended in anhydrous toluene (2700 cc). Ethyl 2-ethyl-3-(pyridazin-3-yl)-3-oxopropionate (215 g) is thus obtained in the form of a green oil.

EXAMPLE 12

Proceeding as in Example 11 but starting with ethyl 2-propyl-3-(pyridazin-3-yl)-3-oxopropionate (109.8 g) and phosphorus pentasulphide (124 g) suspended in toluene (1400 cc), 4-propyl-5-(pyridazin-3: -yl)-1,2-dithiole-3-thione (4.05 g), melting at 77° C. and then 103° C., is obtained after recrystallisation from methanol (50 cc).

Ethyl 2-propyl-3-(pyridazin-3-yl)-3-oxopropionate can be prepared from ethyl (pyridazin-3-yl)-carboxylate (101 g), ethyl valerate (86.5 g) and sodium tert.-butoxide (63.7 g) suspended in dry toluene (1400 cc). Ethyl 2-propyl-3-(pyridazin-3-yl)-3-oxopropionate (133.4 g) is obtained in the form of a brown oil.

EXAMPLE 13

Proceeding as in Example 11 but starting with ethyl-3-(6-dimethylaminopyridazin-3-yl)-2-ethyl-3-oxopropionate (58 g) and phosphorus pentasulphide (73 g) suspended in toluene (1160 cc), 5-(6-dimethylaminopyridazin-3-yl)-4-ethyl-1,2-dithiole-3-thione (5.7 g), melting at 160° C. and then 164° C., is obtained after recrystallisation from 1,2-dichloroethane (38 cc).

Ethyl 3-(6-dimethylaminopyridazin-3-yl)-2-ethyl-3-oxopropionate can be prepared from ethyl (6-dimethylaminopyridazin-3-yl)-carboxylate (57 g), ethyl butyrate (67.7 g) and sodium tert.-butoxide (56 g) suspended in dry toluene (1260 cc). Ethyl 3-(6-dimethylaminopyridazin-3-yl)-2-ethyl-3-oxopropionate (58 g) is obtained in the form of a brown oil.

EXAMPLE 14

A solution of ethyl 3-(6-dimethylaminopyridazin-3-yl)-2-methyl-3-oxopropionate (9.8 g) in toluene (115 cc) is added over a period of 15 minutes to a suspension of phosphorus pentasulphide (12.99 g) in toluene (115 cc) heated to a temperature of about 110° C. The heating under reflux is continued for 45 minutes. After cooling to a temperature of about 20° C., distilled water (230 cc), acetic acid (230 cc) and chloroform (230 cc) are added successively to the reaction mixture. After stirring of this mixture for 20 hours at a temperature of about 20° C., dimethylformamide (50 cc) and potassium carbonate (300 g) are added. The aqueous phase is decanted and washed with chloroform (3 × 100 cc). The combined organic phases are dried over sodium sulphate, filtered and evaporated to dryness under reduced pressure. The residue obtained is dissolved in chloroform (600 cc) and the resulting solution is filtered on silica gel (120 g) in a column 3.5 cm in diameter. The column is eluted with pure chloroform (800 cc). This eluate is discarded. Thereafter the column is eluted with pure chloroform (700 cc) and the corresponding eluate is evaporated to dryness under reduced pressure. 5-(6-Dimethylaminopyridazin-3-yl)-4-methyl-1,2-dithiole-3-thione (1.85 g), melting at 216° C., is obtained.

Ethyl 3-(6-dimethylaminopyridazin-3-yl)-2-methyl-3-oxopropionate can be prepared from ethyl (6-dimethylaminopyridazin-3-yl)-carboxylate (22.8 g), ethyl propionate (11.93 g) and sodium tert.-butoxide (11.23 g) suspended in anhydrous toluene (400 cc). Ethyl 3-(6-dimethylaminopyridazin-3-yl)-2-methyl-3-oxopropionate (9.8 g) is obtained in the form of a brown oil.

Ethyl (6-dimethylaminopyridazin-3-yl)-carboxylate can be obtained by heating a suspension of 3-cyano-6-dimethylaminopyridazine (52.7 g) in a mixture of distilled water (600 cc), 10N sodium hydroxide solution (200 cc) and ethanol (400 cc) at a temperature of about 70° C. for four and a half hours. After cooling to a temperature of about 20° C., methylene chloride (200 cc) is added to the reaction mixture which is allowed to stand for 12 hours at a temperature of about 20° C. The aqueous phase is decanted, acidified with 12N hydrochloric acid (150 cc), and evaporated to dryness under reduced pressure. Ethanol (360 cc), 1,2-dichloroethane (360 cc) and pure methane-sulphonic acid (76 g) are added to the residue thus obtained. The resulting mixture is then heated under reflux for 20 hours. After cooling to a temperature of about 20° C., the insoluble material which has formed is filtered off and washed with methylene chloride (3 × 20 cc). A saturated aqueous sodium carbonate solution (720 cc) is added to the filtrate thus obtained. The resulting insoluble product is filtered off and washed with methylene chloride (2 × 200 cc). The aqueous phase is decanted and washed with methylene chloride (2 × 100 cc). The combined organic fractions are dried over magnesium sulphate, filtered and evaporated to dryness under reduced pressure. Ethyl (6-dimethylaminopyridazin3-yl)-carboxylate (50.81 g), melting at 112° C. is thus obtained.

3-Cyano-6-dimethylaminopyridazine can be prepared by heating a suspension of 3-iodo-6-dimethylaminopyridazine (63.7 g) and cuprous cyanide (34.3 g) in dimethylformamide (380 cc) at a temperature of about 150° C. for 10 minutes. After cooling to a temperature of about 20° C., the reaction mixture is poured into a mixture of distilled water (3,000 cc), methylene chloride (700 cc), ammonium bicarbonate (101 g) and 11N ammonia (115 cc). After stirring of the mixture for 10 minutes at a temperature of about 20° C., the aqueous phase is decanted and washed with methylene chloride (3 × 300 cc). The combined organic phases are dried over magnesium sulphate filtered and evaporated to dryness under reduced pressure. 3-Cyano-6-dimethylaminopyridazine (30.5 g), melting at 150° C., is obtained.

3-Iodo-6-dimethylaminopyridazine can be prepared by stirring a solution of 3,6-diiodopyridazine (203.7 g) and dimethylamine (276 g) in methanol (1500 cc) at a temperature of about 20° C. for 48 hours. After evaporation to dryness under reduced pressure, the residue obtained is stirred for 15 minutes with distilled water (1500 cc). The insoluble product is filtered off and washed with distilled water (2 × 200 cc). 6-Dimethylamino-3-iodopyridazine (113.7 g), melting at 135° C., is obtained.

EXAMPLE 15

A suspension of ethyl 2-ethyl-3-(6-pyrrolidin1'-ylpyridazin-3-yl)-3-oxopropionate (3 g) and phosphorus pentasulphide (3.33 g) in toluene (50 cc) is heated at a temperature of about 105° C. for 1 hour. After cooling to a temperature of about 20° C., the solid residue is filtered off and then stirred for 1 hour with chloroform (100 cc), 11N ammonia (50 cc) and distilled water (50 cc). Thereafter the organic phase is decanted and the aqueous phase is washed with chloroform (2 × 25 cc). The combined organic fractions are dried over magnesium sulphate, filtered and evaporated to dryness under reduced pressure. The residue thus obtained is dissolved in methylene chloride (50 cc) and filtered over silica gel (90 g) contained in a column 2.5 cm in diameter. Thereafter the column is eluted with methylene chloride (300 cc). This eluate is discarded. The column is then eluted with a mixture (300 cc) of methylene chloride and ethyl acetate (95:5 by volume). This eluate is discarded. Finally, the column is eluted with a mixture (650 cc) of methylene chloride and ethyl acetate (95:5 by volume). The corresponding eluate is evaporated to dryness under reduced pressure and the residue obtained is stirred for 5 minutes with diisopropyl ether (15 cc). 4-Ethyl-5-(6-pyrrolidin-1'-ylpyridazin-3-yl)-1,2-dithiole-3-thione (0.5 g), melting at 190° C., is obtained after filtration and drying.

Ethyl 2-ethyl-3-(6-pyrrolidin-1'-ylpyridazin-3-yl)-3-oxopropionate can be prepared from ethyl (6-pyrrolidin-1'-ylpyridazin-3-yl)-carboxylate (5.3 g), ethyl butyrate (5.6 g) and sodium tert.-butoxide (4.6 g) suspended in dry toluene (125 cc). Ethyl 2-ethyl-3-(6-pyrrolidin-1'-ylpyridazin-3-yl)-3-oxopropionate (3 g) is obtained in the form of a yellow oil.

Ethyl (6-pyrrolidin-1'-ylpyridazin-3-yl)-carboxylate can be obtained by heating a suspension of 3-cyano-6-pyrrolidin-1'-ylpyridazine (5.3 g) in a mixture of distilled water (50 cc), 10N sodium hydroxide solution (16.5 cc) and ethanol (50 cc) at a temperature of about 80° C. for 5 hours. After cooling to a temperature of about 20° C., 12N hydrochloric acid (12.5 cc) is added to the reaction mixture. The solution obtained is evaporated to dryness under reduced pressure. Ethanol (30 cc), 1,2-dichloroethane (130 cc) and pure methanesulphonic acid (3.84 g) are added to the residue thus obtained. Thereafter the resulting mixture is heated under reflux for 17 hours. After cooling to a temperature of about 20° C., methylene chloride (200 cc), distilled water (20 cc), sodium bicarbonate (4 g) and magnesium sulphate (100 g) are added. After filtration, the solution is concentrated to dryness under reduced pressure to give ethyl (6-pyrrolidin-1'-ylpyridazin-3-yl)-carboxylate (5.4 g) melting at 134° C.

3-Cyano-6-pyrrolidin-1'-ylpyridazine can be obtained from 3-iodo-6-pyrrolidin-1'-ylpyridazine (123 g) and cuprous cyanide (60 g) suspended in dimethylformamide (670 cc). 3-Cyano-6-pyrrolidin-1'-ylpyridazine (59.2 g), melting at 171°-172° C., is obtained.

3-Iodo-6-pyrrolidin-1'-ylpyridazine can be obtained from 3,6-diiodopyridazine (164 g) and pyrrolidine (87.7 g) suspended in methanol (1000 cc). 3-Iodo-6-pyrrolidin-1'-ylpyridazine (137 g), melting at 148°-150° C., is obtained.

EXAMPLE 16

A solution of ethyl 2-chloro-3-(pyrazin-2-yl)3-oxopropionate (42.8 g) in toluene (90 cc) is added over a period of 15 minutes to a suspension of phosphorus pentasulphide (45.7 g) in toluene (457 cc) heated to a temperature of about 80° C. Thereafter the reaction mixture is heated for four and a half hours at a temperature of about 80° C., and then filtered at this temperature. After cooling to a temperature of about 20° C., the filtrate is washed, by decantation, with an aqueous saturated sodium bicarbonate solution (3 × 150 cc), dried over anhydrous sodium sulphate, filtered and concentrated under reduced pressure to a volume of 200 cc. The resulting solution is filtered over silica gel (400 g) contained in a column 2.5 cm in diameter. The column is eluted with a mixture (1000 cc) of methylene chloride and cyclohexane (9:1 by volume). This eluate is discarded. Thereafter the column is eluted with a mixture (1250 cc) of methylene chloride and cyclohexane (9:1 by volume). The eluate thus obtained is evaporated to dryness under reduced pressure. The solid residue is dissolved in pure methylene chloride (520 cc). This solution is stirred for half an hour with decolourizing charcoal and anhydrous sodium sulphate. After filtration, the solution is evaporated to dryness under reduced pressure. After washing the residue obtained with diisopropyl ether (25 cc) and carbon disulphide (10 cc), 4-chloro-5-(pyrazin-2-yl)-1,2-dithiole-3-thione (1.04 g), melting at 212° C., is isolated.

Ethyl 2-chloro-3-(pyrazin-2-yl)-3-oxopropionate can be prepared by adding sulphuryl chloride (61.2 g) to a solution of ethyl 3-(pyrazin-2-yl)-3-oxopropionate (78 g) in anhydrous methylene chloride (780 cc) at a temperature of about 40° C., over a period of 35 minutes. Thereafter the mixture is heated at a temperature of 40° C. for three and a half hours and then it is cooled to a temperature of about 20° C. Distilled water (500 cc) is added to the reaction mixture which is stirred for half an hour at a temperature of about 20° C. Thereafter the organic phase is decanted, washed with distilled water (250 cc) and dried over sodium sulphate. after filtration and concentration to dryness under reduced pressure, ethyl 2-chloro-3-(pyrazin-2-yl)-3-oxopropionate (77.7 ) is obtained in the form of a yellow oil.

EXAMPLE 17

A suspension of phosphorus pentasulphide (80 g) in xylene (1200 cc) is heated under reflux and then a solution of ethyl 2-methyl-3-oxo-3-(pyrimidin-4-yl)propionate (50 g) in xylene (200 cc) is added over a period of 2 minutes. Refluxing is maintained for 15 minutes, the solvent is evaporated under reduced pressure (20 mm Hg) and then the dry residue is taken up in methylene chloride (1300 cc) and a 5N aqueous ammonia solution (800 cc). The aqueous phase is decanted and washed with methylene chloride (3 × 400 cc). The combined organic phases are dried over anhydrous sodium sulphate, and then filtered over silica gel (1200 g) contained in a column 8.5 cm in diameter. Thereafter the column is eluted with pure methylene chloride (11900 cc). The eluate is discarded. Thereafter the column is eluted with pure methylene chloride (15300 cc). The resulting eluate is evaporated. After washing the residue obtained with diisopropyl ether (80 cc) and then recrystallising from ethanol (500 cc), 4-methyl-5-(pyrimidin-4-yl)-1,2-dithiole-3-thione (3.3 g), melting at 167° C., is obtained.

Ethyl 2-methyl-3-oxo-3-(pyrimidin-4-yl)propionate can be prepared by heating under reflux a suspension of sodium hydride (50 g) (50% in mineral oil) in 1,2-dimethoxyethane (125 cc), and then adding a solution (80 cc) of methyl pyrimidine-4-carboxylate (69 g) and ethyl propionate (51 g) in 1,2-dimethoxyethane (500 cc). When the brisk reaction has terminated, the rest of the solution is added over a period of 6 minutes. Refluxing is maintained for a further 15 minutes until the evolution of gas ceases. The solvent is then evaporated under reduced pressure (20 mm Hg). The dry residue obtained is taken up in iced water (500 cc) and diisopropyl ether (1500 cc). The aqueous phase is acidified to pH 4 and then extracted with diethyl ether (3000 cc). The organic phase is dried over anhydrous sodium sulphate, filtered and evaporated to dryness to give ethyl 2-methyl-3-oxo-3-(pyrimidin-4-yl)propionate (50 g) in the form of a honey-coloured oil.

Methyl pyrimidine-4-carboxylate can be prepared in accordance with Wong et al., J. Org. Chem., 30 2398 (1965).

EXAMPLE 18

Proceeding as in Example 17 but starting with phosphorus pentasulphide (64 g) in xylene (1000 cc) and ethyl 2-ethyl-3-oxo-3-(pyrimidin-4-yl)propionate (55.7 g) in xylene (250 cc), 4-ethyl-5-(pyrimidin-4-yl)-1,2-dithiole-3-thione (1.5 g), melting at 100°–102° C., is obtained.

Ethyl 2-ethyl-3-oxo-3-(pyrimidin-4-yl)propionate can be prepared from sodium hydride (30.8 g) (50 % in mineral oil) in 1,2-dimethoxyethane (75 cc), ethyl pyrimidine-4-carboxylate (44 g) and ethyl butyrate (42.2 g) in 1,2-dimethoxyethane (300 cc). Ethyl 2-ethyl-3-oxo-3-(pyrimidin-4-yl)propionate (30 g) is obtained in the form of an oil.

Ethyl pyrimidine-4-carboxylate can be prepared in accordance with Gortinskaya T.V. et al., J. Chim. Gen. U.S.S.R., 25, 2313 (1955).

EXAMPLE 19

Proceeding as in Example 17 but starting with phosphorus pentasulphide (28 g) in xylene (400 cc) and ethyl 3-(5-bromopyrimidin-4-yl)-2-methyl-3-oxopropionate (24 g) in xylene (100 cc), a product (4.5 g) is obtained which is recrystallised from isopropanol (115 cc). 5-(5-Bromopyrimidin-4-yl)-4-methyl-1,2-dithiole-3-thione (1.8 g), melting at 122° C., is thus obtained.

Ethyl 3-(5-bromopyrimidin-4-yl)-2-methyl-3-oxopropionate can be prepared from sodium hydride (18.9 g) (50% in mineral oil) in 1,2-dimethoxyethane (50 cc), ethyl 5-bromopyrimidine-4-carboxylate (45.6 g) and ethyl propionate (19.8 g) in 1,2-dimethoxyethane (40 cc). Ethyl 3-(5-bromopyrimidin-4-yl)-2-methyl-3-oxopropionate (24 g) is obtained in the form of an oil.

Ethyl 5-bromopyrimidine-4-carboxylate can be prepared by the addition of 5-bromopyrimidine-4-carboxylic acid (45.6 g) to thionyl chloride (450 cc) and dimethylformamide (0.5 cc). The mixture is progressively heated to reflux, which is maintained until the evolution of gas ceases. Thereafter the solution is concentrated to dryness under reduced pressure. The residue is taken up in methylene chloride (100 cc) and then, after cooling in an ice-bath, in ethanol (315 cc). The solution is stirred for one and a half hours at a temperature of about 20° C., and then heated under reflux for 30 minutes. The solution obtained is evaporated to dryness under reduced pressure. The residue is taken up in an 8% (w/v) aqueous sodium bicarbonate solution (200 cc) and diethyl ether (1500 cc). The organic phase is dried over sodium sulphate, filtered and evaporated to dryness under reduced pressure to give ethyl 5-bromopyrimidine-4-carboxylate (31 g), b.p. 87°-90° C./0.15 mm Hg.

5-Bromopyrimidine-4-carboxylic acid can be prepared by heating a suspension of formamidine acetate (416 g) in ethanol (1800 cc) at 45° C., and adding simultaneously, on the one hand, a solution of sodium ethoxide obtained from sodium (138 g) and ethanol (3000 cc) and, on the other hand, a solution of mucobromic acid (516 g) in ethanol (800 cc). The addition is carried out over a period of two hours, the temperature being maintained between 45° C. and 50° C. The reaction mixture is maintained at this temperature for one and a half hours The solution obtained is evaporated to dryness under reduced pressure (20 mm Hg). The residue is taken up in ice-water (1000 cc) and decolourizing charcoal (20 g) is added. After filtration the solution is washed with ethyl acetate (4000 cc). The aqueous phase is decanted and acidified with concentrated 12N hydrochloric acid (500 cc). The insoluble matter is filtered off and the filtrate is extracted with ethyl acetate (10,000 cc). The organic layer is decanted and filtered over silica gel (1000 g). Elution is then carried out with ethanol (5000 cc). The resulting eluate is evaporated to dryness under reduced pressure. After taking up the residue in diethyl ether (250 cc), 5-bromopyrimidine-4-carboxylic acid (74 g), melting at 200° C. with decomposition, is obtained.

EXAMPLE 20

Proceeding as in Example 17 but starting with phosphorus pentasulphide (13.8 g) in xylene (300 cc) and ethyl 2-methyl-3-(5-methylthiopyrimidin-4-yl)-3-oxopropionate (10.3 g) in xylene (100 cc), 4-methyl-5-(5-methylthiopyrimidin-4-yl)-1,2-dithiole-3-thione (1.8 g), melting at 89°-90° C., is obtained after recrystallisation from methylcyclohexane.

Ethyl 2-methyl-3-(5-methylthiopyrimidin-4-yl)-3-oxopropionate can be prepared from sodium hydride (9.9 g) (50% in mineral oil) in 1,2-dimethoxyethane (40 cc), ethyl propionate (11.7 g) and ethyl 5-methylthiopyrimidine-4-carboxylate (18.7 g) in 1,2-dimethoxyethane (160 cc). Ethyl 2-methyl-3-(5-methylthiopyrimidin-4-yl)-3-oxopropionate (19.5 g) is obtained in the form of an oil.

Ethyl 5-methylthiopyrimidine-4-carboxylate can be prepared by heating a solution of 5-bromopyrimidine-4-carboxylic acid (3.4 g) in ethanol (34 cc) and boron trifluoride etherate (7.4 g) under reflux for 20 hours. After concentration to dryness under reduced pressure (20 mm Hg), methylene chloride (50 cc) is added to the residue and neutralisation is effected by the addition of an 8% (w/v) aqueous sodium bicarbonate solution. The aqueous phase is decanted and extracted with methylene chloride (50 cc). The combined organic phases are dried over sodium sulphate, filtered and evaporated under reduced pressure. Ethyl 5-methylthiopyrimidine-4-carboxylate (3.7 g), melting at 99°-100° C., is thus obtained.

5-Methylthiopyrimidine-4-carboxylic acid can be prepared by heating 5-bromopyrimidine-4-carboxylic acid (4.1 g), sodium methoxide (2.43 g) and methylmercaptan (2.16 g) under reflux for four and a half hours in ethanol (30 cc). After evaporation of the resulting solution to dryness under reduced pressure, the residue is dissolved in water (20 cc) and the solution acidified to pH 1 with 12N hydrochloric acid. The precipitate which forms is filtered off and washed with water (15 cc) to give 5-methylthiopyrimidine-4-carboxylic acid (2.8 g) melting at 270° C. with decomposition.

EXAMPLE 21

Proceeding as in Example 17 but starting with phosphorus pentasulphide (6.4 g) in xylene (100 cc) and ethyl 2-methyl-3-oxo-3-(pyrimidin-5-yl)propionate (4 g) in xylene (20 cc), 4-methyl-5-(pyrimidin-5-yl)-1,2-dithiole-3-thione (1.79 g), melting at 184° C., is obtained.

Ethyl 2-methyl-3-oxo-3-(pyrimidin-5-yl)propionate can be prepared from sodium hydride (9.6 g) (50% in mineral oil), ethyl pyrimidine-5-carboxylate (15.2 g) and ethyl propionate (10.2 g). Ethyl 2-methyl-3-oxo-3-(pyrimidin-5-yl)propionate (4 g) is obtained in the form of an oil.

Ethyl pyrimidine-5-carboxylate can be prepared in accordance with E. Godefroi, J. Org. Chem. 27, 2264 (1962).

EXAMPLE 22

The method described in Example 17 is employed but starting with phosphorus pentasulphide (49.3 g) in xylene (750 cc) and ethyl 2-ethyl-3-oxo-3-(pyrimidin-5-yl)propionate (33 g) in xylene (200 cc). After filtration over silica gel and recrystallisation of the product from acetone, 4-ethyl-5-(pyrimidin-5-yl)-1,2-dithiole-3-thione (8.4 g), melting at 150-151° C., is obtained.

Ethyl 2-ethyl-3-oxo-3-(pyrimidin-5-yl)propionate can be prepared from sodium hydride (49.5 g) (50% in mineral oil) in 1,2-dimethoxyethane (125 cc), ethyl pyrimidine-5-carboxylate (71.4 g) and ethyl butyrate (60 g) in 1,2-dimethoxyethane (500 cc). Ethyl 2-ethyl-3-oxo-3-(pyrimidin-5-yl)propionate (40.2 g) is obtained in the form of an oil.

EXAMPLE 23

The method described in Example 17 is employed but starting with ethyl 3-(6-dimethylaminopyrimidin-4-yl)-2-methyl-3-oxopropionate (15.2 g) in toluene (95 cc) and phosphorus pentasulphide (20.6 g) in toluene (290 cc). After heating, extraction and filtration of the methylene chloride solution over silica gel (125 g), a product (580 mg) is obtained which is recrystallized from methylcyclohexane (40 cc). 5-(6-Dimethylaminopyrimidin-4-yl)-4-methyl-1,2-dithiole-3-thione (250 mg), melting at 137° C., is thus obtained.

Ethyl 3-(6-dimethylaminopyrimidin-4-yl)-2-methyl-3-oxopropionate can be prepared in the following way:

A solution of 6-dimethylamino-4-ethoxycarbonylpyrimidine (19.5 g) and ethyl propionate (11.2 g) in 1,2-dimethoxyethane (75 cc) is added to a suspension of sodium hydride (9.6 g) (50% in mineral oil) in 1,2-dimethoxyethane (25 cc), and the reaction mixture is refluxed. Refluxing is maintained for a further 30 minutes. The solvent is evaporated, and then the residue is taken up in diethyl ether (350 cc) and 4N hydrochloric acid (70 cc). After decanting, the aqueous phase is again extracted with diethyl ether (450 cc). The combined organic phases are washed with an 8% (w/v) sodium bicarbonate solution (120 cc). They are dried over anhydrous magnesium sulphate, filtered and concentrated to dryness under reduced pressure to give ethyl 3-(6-dimethylaminopyrimidin-4-yl)-2-methyl-3-oxopropionate (15.2 g).

6-Dimethylamino-4-ethoxycarbonylpyrimidine can be prepared in the following way:

Thionyl chloride (740 cc) is added to 4-carboxy-6-dimethylaminopyrimidine (73.6 g) and then the reaction mixture is progressively heated to reflux. Refluxing is maintained for a further one and a half hours. After evaporation of the volatile materials, the residue is taken up in methylene chloride (560 cc). The solution is cooled in an ice-bath and ethanol (1250 cc) is added. Thereafter the volatile materials are distilled off and the residue is taken up in ethyl acetate (600 cc). An 8% (w/v) sodium bicarbonate solution (60 cc), followed by sodium bicarbonate powder, are then added to give a pH of 6. The mixture is decanted and the aqueous layer washed with ethyl acetate (1500 cc). The organic phases are dried over anhydrous magnesium sulphate, filtered and concentrated to dryness under reduced pressure. The resulting residue is dissolved in methylene chloride (400 cc) and filtered over silica gel (450 g). Elution is carried out with methylene chloride (12 liters). The eluates are concentrated under reduced pressure. 6-Dimethylamino-4-ethoxycarbonylpyrimidine (75.5 g), melting at 40°–42° C., is thus obtained.

4-Carboxy-6-dimethylaminopyrimidine can be prepared in the following way:

A 40% aqueous dimethylamine solution (2000 cc) is added to 4-carboxy-6-chloropyrimidine (93.6 g). The mixture is allowed to stand for 3 days and then concentrated to dryness under reduced pressure. The residue is dissolved in water (300 cc). The solution is made alkaline by the addition of sodium bicarbonate powder to a pH of 8 to 9. The solution is then extracted with diisopropyl ether (1000 cc). The aqueous phase is acidified with 12N hydrochloric acid to a pH of 2 to 3. The precipitate is filtered off, washed with ice-water (30 cc) and then with isopropanol (120 cc). 4-Carboxy-6-dimethylaminopyrimidine (73.6 g), melting at 250° C., is obtained.

4-Carboxy-6-chloropyrimidine can be obtained in accordance with V. M. Cherkasov et al., Khim.Get.Soed. 1972, (4) 556 [Chem. Abstr. vol. 77, 61178a (1972)].

EXAMPLE 24

The method as described in Example 17 is employed but starting with ethyl 3-(5-chloropyrimidin-4-yl)-2-methyl-3-oxopropionate (16.2 g) in xylene (165 cc) and phosphorus pentasulphide (22 g) in xylene (270 cc). After filtration of the methylene chloride solution over silica gel (1000 g), a product is obtained which is recrystallised from methylcyclohexane (20 cc). 5-(5-Chloropyrimidin-4-yl)-4-methyl-1,2-dithiole-3-thione (450 mg), melting at 100° C., is thus obtained.

Ethyl 3-(5-chloropyrimidin-4-yl)-2-methyl-3-oxopropionate can be prepared by operating as in the previous Example but starting with sodium hydride (7.9 g) (50% in mineral oil) in 1,2-dimethoxyethane (50 cc), 5-chloro-4-ethoxycarbonylpyrimidine (15.2 g) and ethyl propionate (8.5 g) in 1,2-dimethoxyethane (150 cc). Ethyl 3-(5-chloropyrimidin-4-yl)-2-methyl-3-oxopropionate (18 g) is obtained.

5-Chloro-4-ethoxycarbonylpyrimidine can be prepared by treating 5-chloro-4-carboxypyrimidine (40 g) with ethanol (400 cc) and boron trifluoride etherate (80 cc). After heating for 24 hours under reflux, the volatile materials are eliminated and then methylene chloride (250 cc) is added. An 8% (w/v) aqueous sodium bicarbonate solution (100 cc) is added and then the pH is adjusted to 6 by the addition of sodium bicarbonate powder. A further extraction is carried out with methylene chloride (300 cc). The solvent is evaporated off and then the residue distilled. 5-Chloro-4-ethoxycarbonylpyrimidine (23 g), b.p. 132°–133° C./33 mm Hg, is obtained.

4-Carboxy-5-chloropyrimidine can be prepared in the following way:

Sodium methoxide (162 g) is added to a solution of mucochloric acid (169 g) and formamidine acetate (208 g) in methanol (3 liters) over the course of 20 minutes, and the reaction mixture is heated for 1 hour at 35°–40° C., and then for one and a half hours under reflux. The solvent is removed and water (500 cc) is added to the residue. The aqueous mixture is extracted with ethyl acetate (2 liters). The aqueous phase is brought to pH 1 by the addition of concentrated hydrochloric acid, and the aqueous phase is extracted with ethyl acetate (5 liters). The organic phase is dried over anhydrous magnesium sulphate, filtered and then concentrated to dryness. The residue is washed with diethyl ether (300 cc) and then with diisopropyl ether (600 cc). 4-Carboxy-5-chloropyrimidine (55.6 g), melting at 190° C., is obtained.

EXAMPLE 25

The method as described in Example 17 is employed but starting with phosphorus pentasulphide (8 g) in xylene (100 cc) and ethyl 3-(5-methoxypyrimidin-4-yl)-2-methyl-3-oxopropionate (5.7 g) in xylene (30 cc). After heating, extraction and filtration of the solution in methylene chloride over silica gel (200 g), elution is carried out with methylene chloride (2.2 liters). This eluate is discarded. Elution is then carried out with methylene chloride (500 cc). This eluate is concentrated to dryness and the residue is recrystallised from methylcyclohexane (30 cc) to give 5-(5-methoxypyrimidin-4-yl)-4-methyl-1,2-dithiole-3-thione (350 mg), melting at 136° C.

Ethyl 3-(5-methoxypyrimidin-4-yl)-2-methyl-3-oxopropionate can be prepared by operating as in Example 23 but starting with sodium hydride (3.65 g) (50% in mineral oil) in 1,2-dimethoxyethane (25 cc) and with 5-methoxy-4-methoxycarbonylpyrimidine (5.9 g) and ethyl propionate (4 g) in 1,2-dimethoxyethane (75 cc). Ethyl 3-(5-methoxypyrimidin-4-yl)-2-methyl-3-oxopropionate (5.9 g) is obtained.

4-Methoxycarbonyl-5-methoxypyrimidine can be prepared by heating 5-chloro-4-ethoxycarbonylpyrimidine (23 g) with sodium methoxide (15 g) in methanol (230 cc) for 8 hours. The solvent is evaporated off and the residue is suspended in diethyl ether (1000 cc). The suspension is washed with water (50 cc). The organic phase is dried over sodium sulphate, filtered and concentrated to dryness to give 5-methoxy-4-methoxycarbonylpyrimidine (6 g) melting at 75° C.

EXAMPLE 26

A suspension of phosphorus pentasulphide (49.5 g) in xylene (600 cc) is heated under reflux, and then a solution of ethyl 2-methyl-3-(2-methylthiopyrimidin-4-yl)-3-oxopropionate (47 g) in xylene (100 cc) is added over a period of 2 minutes. The suspension obtained is heated for 10 minutes at a temperature of about 135° C., then phosphorus pentasulphide (40 g) is added and the heating is maintained for a further 5 minutes at 135° C. After decantation of the solution, the residue is washed with xylene (250 cc) at 20° C. The combined xylene phases are cooled to a temperature of about 20° C., a mixture of ice-water (500 cc) and 4N ammonia (200 cc) is added, and the mixture is stirred for 15 minutes at a temperature of about 20° C. The aqueous phase is decanted and washed with xylene (250 cc). The combined organic phases are washed with water (3 × 500 cc), dried over magnesium sulphate, filtered and evaporated to dryness under reduced pressure (30 mm Hg). The residue is taken up in acetone (50 cc) at 20° C. The precipitate thus obtained is filtered off and dried to give 4-methyl-5-(2-methylthiopyrimidin-4-yl)-1,2-dithiole-3-thione (4.47 g) melting at 170°–172° C. After recrystallisation from acetonitrile, the product melts at 177°–178° C.

Ethyl 2-methyl-3-(2-methylthiopyrimidin-4-yl)-3-oxopropionate can be prepared by heating a solution of methyl 2-methylthiopyrimidine-4-carboxylate (36.8 g) in ethyl propionate (250 cc) to reflux whilst adding sodium hydride (6 g) (50% in mineral oil) in small portions over a period of 12 minutes. After the heating is stopped, toluene is added (250 cc) and then sodium hydride (5.5 g) in small portions over a period of 12 minutes. The temperature of the reaction mixture is 55° C. The mixture is heated to a temperature of about 95° C., and then allowed to cool. The reaction mixture is poured into a mixture of 5N hydrochloric acid (75 cc) and ice and water (1000 cc). After stirring for 10 minutes, the aqueous phase is decanted and washed with diisopropyl ether (2 × 250 cc). The organic phases are combined and washed with water (2 × 250 cc). The organic phase is dried over magnesium sulphate. After filtration and concentration to dryness under reduced pressure (30 mm Hg), ethyl 2-methyl-3-(2-methylthiopyrimidin-4-yl)-3-oxopropionate (47.5 g) is obtained in the form of a chestnut-red oil.

Methyl 2-methylthiopyrimidine-4-carboxylate can be prepared by hydrogenolysis of methyl 6-chloro-2-methylthiopyrimidine-4-carboxylate (184 g) in methanol (2000 cc) in the presence of palladium on charcoal (55 g) (containing 3% by weight of palladium) and triethylamine (147.5 cc). Hydrogenation is carried out at 25° C. under a pressure of 6100 mm Hg for 6 hours. The catalyst is filtered off and washed with methanol (2 × 100 cc). The methanolic solutions are combined and evaporated to dryness under reduced pressure (30 mm Hg). The residue is taken up in water (500 cc) and ethyl acetate (500 cc). The aqueous phase is decanted and washed with ethyl acetate (4 × 250 cc). The combined organic phases are washed with water (2 × 100 cc), dried over magnesium sulphate in the presence of decolourizing charcoal, filtered and evaporated to dryness under reduced pressure (30 mm Hg). The residue is recrystallised from diisopropyl ether (300 cc) to give methyl 2-methylthiopyrimidine-4-carboxylate (111 g) melting at 68° C.

Methyl 6-chloro-2-methylthiopyrimidine-4-carboxylate can be prepared in accordance with G. D. Daves, Jr. et al., J. Org. Chem., 26, 2755–63 (1961).

EXAMPLE 27

Ethyl 3-(2-dimethylaminopyrimidin-5-yl)-2-methyl-3-oxopropionate (4.2 g) in solution in anhydrous xylene (10 cc) is added to a boiling suspension of phosphorus pentasulphide (2.66 g) in anhydrous xylene (50 cc) over a period of about one minute. Heating under reflux is continued for 6 minutes after the end of the addition, and then the solvent is evaporated under reduced pressure (30 mm Hg). The resulting residue is taken up in methylene chloride (50 cc) and a 2N aqueous ammonia solution (40 cc). After stirring, the organic phase is decanted and the aqueous phase is extracted with methylene chloride (3 × 50 cc). The combined methylene chloride phases are washed with distilled water (2 × 25 cc), dried over magnesium sulphate, filtered and concentrated to dryness under reduced pressure (30 mm Hg). The red-brown oily residue is taken up in methylene chloride (20 cc) and then it is filtered over silica gel (50 g) contained in a column 1.6 cm in diameter. The column is eluted with methylene chloride. The eluate is discarded when it is not coloured, and then elution is carried out with methylene chloride (220 cc). This eluate is discarded. A further elution is carried out with methylene chloride (800 cc) and the corresponding eluate is evaporated to dryness under reduced pressure (30 mm Hg). The resulting residue is taken up in hexane (10 cc) at 20° C., filtered, washed with hexane at 20° C., and dried under reduced pressure to give 5-(2-dimethylaminopyrimidin-5-yl)-4-methyl-1,2-dithiole-3-thione (0.18 g) melting at 135° C.

Ethyl 3-(2-dimethylaminopyrimidin-5-yl)-2-methyl-3-oxopropionate can be prepared by adding sodium hydride (0.57 g) (50% in mineral oil) to a solution of ethyl 2-dimethylaminopyrimidine-5-carboxylate (1.95 g) in boiling anhydrous ethyl propionate (20 cc) over a period of 3 minutes. Heating under reflux is continued for 1 hour 15 minutes and then the reaction mixture is allowed to cool to a temperature of about 20° C. Thereafter a 0.4N iced aqueous hydrochloric acid solution (55 cc) and ethyl acetate (50 cc) are added, followed by a saturated aqueous sodium bicarbonate solution (10 cc) at 20° C. in order to adjust the pH to 8. The organic phase is decanted and then the aqueous phase is extracted with ethyl acetate (2 × 50 cc). The combined organic phases are washed with distilled water (2 × 25 cc), dried over magnesium sulphate, filtered and then concentrated to dryness under reduced pressure (30 mm Hg) to give crude ethyl 3-(2-dimethylaminopyrimidin-5-yl)-2-methyl-3-oxopropionate (4.2 g).

Ethyl 2-dimethylaminopyrimidine-5-carboxylate can be prepared by adding zinc powder (65 g) over a period of 10 minutes to a refluxing solution of ethyl 6-chloro-2-dimethylaminopyrimidine-5-carboxylate (23 g) in a mixture of ethanol (500 cc) and distilled water (100 cc). Heating under reflux is continued for 24 hours, the reaction mixture is filtered hot, and rinsed with ethanol (2 × 50 cc) and then with distilled water (50 cc). Thereafter the filtrate is concentrated to dryness under reduced pressure. The pasty residue is taken up in distilled water (100 cc). The product which crystallises is filtered off and washed with distilled water (2 × 15 cc) and dried under reduced pressure. Ethyl 2-dimethylaminopyrimidine-5-carboxylate (12.04 g) melting at 65° C., is thus obtained.

Ethyl 6-chloro-2-dimethylaminopyrimidine-5-carboxylate can be prepared in accordance with German Patent Application No. 2406930.

EXAMPLE 28

A solution of ethyl 3-(6-methoxypyridazin-3-yl)-2-methyl-3-oxopropionate (184.5 g) in toluene (1000 cc) is added over a period of 10 minutes to a suspension of phosphorus pentasulphide (155 g) in toluene (1000 cc) heated to reflux. The reaction mixture is kept under reflux for 30 minutes. After cooling the reaction mixture to a temperature of about 80° C., the supernatant solution is removed. The precipitate is taken up in toluene (250 cc) at a temperature of about 80° C. The toluene solution is separated from the precipitate. The toluene phases, cooled to a temperature of about 20° C., are combined, washed with distilled water (4 × 500 cc), a 10% (w/v) aqueous potassium bicarbonate solution (2

× 500 cc) and distilled water (5 × 500 cc), dried over magnesium sulphate, filtered and evaporated to dryness under reduced pressure (30 mm Hg).

The residue is taken up in toluene (200 cc) at a temperature of about 20° C. A product precipitates which is filtered off and washed with toluene (3 × 20 cc), distilled water (3 × 15 cc) and diisopropyl ether (4 × 10 cc). 5-(6-Mercaptopyridazin-3-yl)-4-methyl-1,2-dithiole-3-thione (1.4 g), melting at 245° C., is thus obtained.

Toluene (1300 cc) is added to the toluene solution obtained previously after filtration of the precipitate, and the solution is then heated under reflux. Thereafter phosphorus pentasulphide (173 g) is added in portions over a period of 45 minutes. Refluxing is maintained for 10 minutes. After treatment of the toluene solution at 80° C. as described before, 5-(6-mercaptopyridazin-3-yl)-4-methyl-1,2-dithiole-3-thione (6.1 g), melting at 245° C., is obtained.

Ethyl 3-(6-methoxypyridazin-3-yl)-2-methyl-3-oxopropionate is prepared by the fractional addition, over a period of 20 minutes, of sodium hydride (19.2 g) (50% in mineral oil) to a solution of methyl 6-methoxypyridazine-3-carboxylate (50 g) in ethyl propionate (220 g) at a temperature of about 98° C. The reaction mixture is maintained under reflux for a further 30 minutes. It is subsequently cooled to a temperature of about 20° C., and ethanol (10 cc) is added with care, followed by distilled water (800 cc). The aqueous phase is removed, washed by decantation with diisopropyl ether (3 × 250 cc), pure acetic acid (250 cc) is added (pH = 5–6) and the aqueous phase is washed again with ethyl acetate (3 × 150 cc). The organic phase are combined, dried over magnesium sulphate, filtered and evaporated to dryness under reduced pressure (30 mm Hg) to give ethyl 3-(6-methoxypyridazin-3-yl)-2-methyl-3-oxopropionate (37.2 g) in the form of a yellow oil.

Methyl 6-methoxypyridazine-3-carboxylate can be prepared in accordance with T. Nakagome et al., J. Het. Chem., p. 379 (1968).

EXAMPLE 29

Proceeding as in Example 4 but starting with ethyl 4-ethoxycarbonyl-5-(pyridazin-2-yl)-5-oxopentanoate (69.8 g), phosphorus pentasulphide (57.9 g) and pyridine (580 cc), ethyl 3-[5-(pyrazin-2-yl)-3-thioxo-1,2-dithiol-4-yl]-propionate (3.26 g), melting at 77° C., is obtained after recrystallization from cyclohexane (130 cc).

Ethyl 4-ethoxycarbonyl-5-(pyrazin-2-yl)-5-oxopentanoate can be prepared from ethyl 3-(pyrazin-2-yl)-3-oxopropionate (77.6 g), ethyl β-chloropropionate (67 g), potassium iodide (66.4 g) and dry potassium carbonate (50.8 g) suspended in acetone (500 cc). Ethyl 4-ethoxycarbonyl-5-(pyrazin-2-yl)-5-oxopentanoate (77 g) is obtained in the form of an orange oil.

EXAMPLE 30

Proceeding as in Example 4 but starting with ethyl 3-ethoxycarbonyl-4-(pyrazin-2-yl)-4-oxobutyrate (364 g) and phosphorus pentasulphide (159 g) in pyridine (1600 cc), ethyl [5-(pyrazin-2-yl)-3-thioxo-1,2-dithiol-4-yl]-acetate (16.7 g), melting at 119° C., is obtained after recrystallisation from ethanol (300 cc).

Ethyl 3-ethoxycarbonyl-4-(pyrazin-2-yl)-4-oxobutyrate can be prepared by adding, over a period of 5 minutes at a temperature of about 35° C., a solution of 2-ethoxycarbonylpyrazine (228 g) and ethyl succinate (261 g) in anhydrous toluene (700 cc) to a suspension of sodium tert.-butoxide (144 g) in anhydrous toluene (300 cc). Thereafter the reaction mixture is stirred for 12 hours at a temperature of about 20° C., and then 12N hydrochloric acid (130 cc) and distilled water (1300 cc) are added. The organic phase is decanted, washed with distilled water (500 cc) and then dried over magnesium sulphate. After filtration and concentration to dryness under reduced pressure, ethyl 3-ethoxycarbonyl-4-(pyrazin-2-yl)-4-oxobutyrate (364 g) is obtained in the form of a red oil.

EXAMPLE 31

A solution of ethyl pyrazinoylmalonate (37.5 g) in toluene (130 cc) is added to a suspension of phosphorus pentasulphide (34.2 g) in toluene (430 cc) heated under reflux. The reaction mixture is then heated under reflux for one hour, and filtered whilst boiling. The insoluble product is washed with boiling toluene (4 × 100 cc). The filtrate and the cooled washings are successively washed with an aqueous saturated sodium bicarbonate solution (3 × 100 cc) and then with water (100 cc). The organic solution obtained is dried with anhydrous sodium sulphate, treated with decolourizing charcoal and then evaporated to dryness under reduced pressure (20 mm Hg). By recrystallization of the residue obtained from ethyl acetate (50 cc), 4-ethoxycarbonyl-5-(pyrazin-2-yl)-1,2-dithiole-3-thione (7.5 g), melting at 125° C. and then at 134° C., is obtained.

Ethyl pyrazinoylmalonate can be prepared by adding a solution of pyrazinoyl chloride (135 g; 0.95 mol) in anhydrous diethyl ether (2000 cc) to a diethyl ether solution of ethyl ethoxymagnesium malonate (1.045 mol) (prepared in accordance with the method described in Org. Synth. Coll. Vol. 4, 285). The reaction mixture is then heated under reflux for one hour and, after cooling, it is poured into water (3000 cc). Thereafter ethyl acetate (1500 cc) is added, the mixture is acidified to pH 1 by the addition of 10N hydrochloric acid and stirred for 2 hours at a temperature of about 20° C. until the complete disappearance of the insoluble material. The aqueous layer is then decanted and washed with ethyl acetate (2 × 500 cc). The organic layers are combined, washed with water (500 cc) and then successively extracted with a 20% (w/v) aqueous potassium carbonate solution (1 × 1000 cc and 3 × 500 cc). These aqueous layers are washed by decantation with ethyl acetate (500 cc) and then acidified to pH 2 by the addition of 10N hydrochloric acid. The product which is rendered insoluble is extracted with ethyl acetate (3 × 2000 cc), and then the organic layers are decanted, combined, dried over sodium sulphate and evaporated to dryness under reduced pressure. Ethyl pyrazinoylmalonate (211 g), melting at 54° C., is thus obtained.

Pyrazinoyl chloride can be prepared in accordance with the method described in I. A. Salomons and P. E. Spoerri, J. Amer. Chem. Soc., 75, 679 (1953).

EXAMPLE 32

A solution of 4-ethoxycarbonyl-5-(pyrazin-2-yl)-1,2-dithiole-3-thione (150 g) [prepared as described in Example 31] in acetic acid (6750 cc), concentrated sulphuric acid (515 cc) and water (515 cc) is heated for 2 hours under reflux. After cooling, the product which crystallises is filtered off and washed successively with acetic acid (100 cc) and carbon disulphide (2 × 100 cc). This product is then suspended in water (1350 cc) and stirred for 48 hours at a temperature of about 20° C. The insoluble product is then filtered off and washed with water (2 × 250 cc). After drying, 4-carboxy-5-(pyrazin- 2-yl)-1,2-dithiole-3-thione (97.5 g), melting at 225° C., is obtained.

EXAMPLE 33

A suspension of 4-carboxy-5-(pyrazin-2-yl)-1,2-dithiole-3-thione (12.8 g) [prepared as described in Example 32] and 1-ethoxycarbonyl-2-ethoxy-1,2-dihydroquinoline (13.25 g) in methylene chloride (40 cc) is stirred for 5 hours at a temperature of about 20° C. A solution (15 c) of 4N ammonia in methanol is added over a period of 10 minutes to the solution obtained, and the reaction mixture is stirred for a further 5 minutes at a temperature of about 20° C. The insoluble product is filtered off and washed successively with methylene chloride (50 cc), saturated aqueous sodium bicarbonate solution (25 cc), water (4 × 100 cc) and then ethyl acetate (15 cc). The residue obtained is dissolved at a temperature of about 100° C. in dimethylformamide (100 cc) and the solution, which is filtered hot, is then poured into distilled water (200 cc). After cooling to a temperature of about 20° C., the insoluble product is filtered off and washed with ethyl acetate (2 × 10 cc) to give 4-carbamoyl-5-(pyrazin-2-yl)-1,2-dithiole-3-thione (6.58 g) melting at 267° C.

EXAMPLE 34

A solution of ethyl chloroformate (5.43 g) in anhydrous dimethylformamide (25 cc) is added to a solution of 4-carboxy-5-(pyrazin-2-yl)-1,2-dithiole-3-thione (12.8 g) [prepared as described in Example 32] and triethylamine (6.3 g) in anhydrous dimethylformamide (128 cc) cooled to a temperature of about −50° C. The reaction mixture is maintained for one hour at a temperature of about 0° C., then butylamine (3.65 g) is added to it, and the solution is allowed to return to a temperature of about 20° C. until the evolution of gas ceases. Thereafter the reaction mixture is poured into water (750 cc). The product which is rendered insoluble is filtered off, washed with water (15 cc), drained and then dissolved in methylene chloride (500 cc). The resulting solution is dried over anhydrous magnesium sulphate and then evaporated to dryness under reduced pressure. By recrystallisation of the residue from acetonitrile (100 cc), 4-butylcarbamoyl-5-(pyrazin-2-yl)-1,2-dithiole-3-thione (6 g), melting at 178° C., is obtained.

EXAMPLE 35

1-Ethoxycarbonyl-2-ethoxy-1,2-dihydroquinoline (2.65 g) is added, at a temperature of about 20° C., to a suspension of 4-carboxy-5-(pyrazin-2-yl)-1,2-dithiole-3-thione (2.56 g) (prepared as described in Example 32) and butylamine (0.73 g) in anhydrous methylene chloride (80 cc). The reaction mixture is then stirred for 4 hours at a temperature of about 20° C. The solid residue is filtered off and the filtrate is evaporated to dryness under reduced pressure. After recrystallisation of the residue from acetonitrile (50 cc), 4-butylcarbamoyl-5-(pyrazin-2-yl)-1,2-dithiole-3-thione (1 g), melting at 179° C., is obtained.

EXAMPLE 36

A solution of 4-carboxy-5-(pyrazin-2-yl)-1,2-dithiole-3-thione (10.24 g) (prepared as described in Example 32) in butanol (400 cc) and 36N sulphuric acid (20 cc) is heated under reflux for 6 hours. The product which crystallises on cooling is filtered off and washed successively with ethanol (3 × 10 cc) and then diisopropyl ether (3 × 20 cc). By recrystallisation of this product from acetonitrile (80 cc), 4-butoxycarbonyl-5-(pyrazin-2-yl)-1,2-dithiole-3-thione (6.1 g), melting at 130° C., is obtained.

EXAMPLE 37

Anhydrous hexamethylphosphotriamide (5 cc) and 4-carboxy-5-(pyrazin-2-yl)-1,2-dithiole-3-thione (1.28 g) (prepared as described in Example 32) are added to a solution of dry sodium ethoxide (0.34 g) in anhydrous ethanol (5 cc). The suspension obtained is heated to a temperature of about 50° C., the resulting solution is cooled to a temperature of about 20° C. and then butyl iodide (1.7 g) is added. The reaction mixture is then maintained at a temperature of about 50° C. for 7 hours. An insoluble material is filtered off and the filtrate is evaporated to dryness under reduced pressure (20 mm Hg). The oil obtained is treated with ethyl acetate (2 cc) and the product which crystallises is filtered off and washed with diethyl ether (2 cc). After drying, 4-butoxycarbonyl-5-(pyrazin-2-yl)-1,2-dithiole-3-thione (0.4 g), melting at 127° C., is obtained.

EXAMPLE 38

A suspension of 4-(2,2-diethoxyacetoxy-methyl). 5-(pyrazin-2-yl)-1,2-dithiole-3-one (3.56 g) and phosphorus pentasulphide (2.22 g) in dioxan (100 cc) is heated for 15 minutes at a temperature of about 100° C. After cooling to a temperature of about 20° C., distilled water (200 cc) and methylene chloride (200 cc) are added to the reaction mixture. The organic phase is decanted, washed with distilled water (100 cc) and evaporated to dryness under reduced pressure. 1,2-Dichloroethane (50 cc), distilled water (10 cc) and 36N sulphuric acid (10 cc) are added to the residue thus obtained, and the resulting mixture is heated for 10 minutes at a temperature of about 85° C. After cooling to a temperature of about 20° C., distilled water (100 cc) and methylene chloride (50 cc) are added. The aqueous phase is decanted and washed with methylene chloride (3 × 25 cc). The combined organic fractions are washed with an aqueous saturated sodium bicarbonate solution (25 cc), dried over magnesium sulphate, filtered and evaporated to dryness under reduced pressure. After two successive recrystallisations from acetic acid, 4-hydroxymethyl-5-(pyrazin-2-yl)-1,2-dithiole-3-thione (0.14 g), melting at 200° C., is obtained.

4-(2,2-Diethoxyacetoxy-methyl)-5-(pyrazin-2-yl)-1,2-dithiole-3-one can be prepared by heating a suspension of 4-bromomethyl-5-(pyrazin-2-yl)-1,2-dithiole-3-one (2 g) and sodium 2,2-diethoxyacetate (1.31 g) in acetone (100 cc) for half an hour at a temperature of about 50° C. After cooling to a temperature of about 20° C., reaction mixture is evaporated to dryness under reduced pressure. Distilled water (25 cc) and methylene chloride (50 cc) are added to the residue thus obtained. The aqueous phase is decanted and washed with methylene chloride (2 × 25 cc). The combined organic fractions are washed by decantation with distilled water (2 × 20 cc), dried over magnesium sulphate, filtered and evaporated to dryness under reduced pressure. The residue thus obtained is dissolved in methylene chloride (100 cc) and filtered over silica gel (40 g) contained in a column 2.2 cm in diameter. The column is eluted with pure methylene chloride (550 cc). This eluate is discarded. Thereafter the column is eluted with pure methylene chloride (800 cc). The corresponding eluate is evaporated to dryness under reduced pressure to give 4-(2,2-diethoxyacetoxy-methyl)-5-(pyrazin-2-yl)-1,2-dithiole-3-one (1.3 g) melting at 74°-76° C.

4-Bromomethyl-5-(pyrazin-2-yl)-1,2-dithiole-3-one can be prepared by heating a suspension of 4-methyl-5-(pyrazin-2-yl)-1,2-dithiole-3-one (2.1 g), N-bromosuccinimide (1.8 g) and azobisisobutyronitrile (0.16 g) in anhydrous carbon tetrachloride (30 cc) for six and a half hours at a temperature of about 75° C. After cooling to a temperature of about 20° C., methylene chloride (50 cc) is poured into the reaction mixture and the insoluble material is filtered off, and washed with methylene chloride (2 × 25 cc). The filtrate and the washings are combined and evaporated to dryness under reduced pressure. After recrystallisation of the residue thus obtained from acetonitrile (50 cc), 4-bromomethyl-5-(pyrazin-2-yl)-1,2-dithiole-3-one (1.1 g), melting at 153° C., is obtained.

4-Methyl-5-(pyrazin-2-yl)-1,2-dithiole-3-one can be prepared by heating a suspension of 4-methyl-5-(pyrazin-2-yl)-1,2-dithiole-3-thione (14.7 g) [prepared as described in Example 2] and mercuric aceate (31.06 g) in acetic acid (650 cc) for one and a half hours at a temperature of about 100° C. After cooling to a temperature of about 20° C., the insoluble product is filtered off and washed with acetic acid (2 × 100 cc). The filtrate and the washings are combined and concentrated to dryness under reduced pressure. The solid residue obtained is taken up in acetone (250 cc). The resulting suspension is stirred for 1 hour at a temperature of about 20° C., and the insoluble material is then filtered off and washed with acetone (4 × 50 cc). The filtrate and the washings are combined and concentrated to dryness under reduced pressure. After recrystallisation of the residue from ethanol (300 cc), 4-methyl-5-(pyrazin-2-yl)-1,2-dithiole-3-one (11.1 g), melting at 119° C., is obtained.

The present invention includes within its scope pharmaceutical compositions which comprise, as active ingredient, at least one 1,2-dithiole derivative of general formula I in association with one or more compatible and pharmaceutically acceptable diluents or adjuvants, and optionally other compatible and physiologically active products. The invention includes especially such preparations made up for oral, parenteral or rectal administration.

Solid compositions for oral administration include tablets, pills, powders, gelatin-coated pills or granules. In such solid compositions the active compound is admixed with at least one inert diluent such as sucrose, lactose or a starch. The compositions may also comprise, as is normal practice, additional substances other than inert diluents, e.g. lubricating agents such as magnesium stearate, or a wetting agent. Liquid compositions for oral administration include pharmaceutically-acceptable emulsions, solutions, suspensions, syrups and elixirs containing inert diluents commonly used in the art, such as water and liquid paraffin. Besides inert diluents such compositions may also comprise adjuvants, such as wetting, emulsifying and suspending agents, and sweetening, flavouring and aromatizing agents. The compositions according to the invention, for oral administration, also include capsules of absorbable material such as gelatin containing the active substance with or without the addition of diluents or excipients.

Compositions according to the invention for parenteral administration include sterile aqueous or non-aqueous solutions, suspensions or emulsions. Examples of non-aqueous solvents or vehicles are propylene glycol, polyethylene glycol, vegetable oils such as olive oil, and injectable organic esters such as ethyl oleate. These compositions may also contain adjuvants such as preserving, wetting, emulsifying and dispersing agents. They may be sterilized by, for example, filtration through a bacteria-retaining filter, by incorporation in the compositions of sterilizing agents, by irradiation, or by heating. They may also be manufactured in the form of sterile solid compositions, which can be dissolved in sterile water or some other sterile injectable medium immediately before use.

Compositions for rectal administration are suppositories which contain, in addition to the active substance, excipients such as cacao butter or a suitable wax base.

In human therapy the compositions are particularly useful in the treatment of bilharziasis.

The percentage of active ingredient in the compositions of the invention may be varied, it being necessary that it should constitute a proportion such that a suitable dosage shall be obtained. The dosage depends on the desired therapeutic effect, on the route of administration and on the duration of the treatment. In human therapy the compositions when administered to an adult should generally give doses between 10 mg and 100 mg/kg body weight of active substance per day orally, and between 1 and 50 mg/kg body weight of active substance per day parenterally. In general the physician will decide the posology considered appropriate, taking into account the age and weight and other factors intrinsic to the patient being treated.

The following Examples illustrate pharmaceutical compositions according to the invention.

EXAMPLE 39

Tablets containing 100 mg of active product, and having the following composition, are prepared in accordance with the usual technique:

| | |
|---|---|
| 4-methyl-5-(pyrazin-2-yl)-1,2-dithiole-3-thione | 100 mg |
| starch | 100 mg |
| precipitated silica | 45 mg |
| magnesium stearate | 5 mg. |

EXAMPLE 40

Tablets containing 100 mg of active product, and having the following composition, are prepared in accordance with the usual technique:

| | |
|---|---|
| ethyl [5-(pyrazin-2-yl)-3-thioxo-1,2-dithiol-4-yl]-acetate | 100 mg |
| starch | 100 mg |
| precipitated silica | 45 mg |
| magnesium stearate | 5 mg. |

We claim:
1. A 1,2-dithiole of the formula:

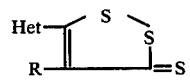

wherein Het represents pyrimidin-2-yl, pyrimidin-4-yl, or pyrimidin-5-yl, or a said pyrimidin-2-yl, pyrimidin-4-yl or pyrimidin-5-yl substituted by halogen, alkyl of 1 through 4 carbon atoms, alkoxy of 1 through 4 carbon atoms, mercapto, alkylthio of 1 through 4 carbon atoms, or dialkylamino having 1 through 4 carbon atoms in each alkyl, and R represents halogen, alkyl of 1 through 4 carbon atoms, alkyl of 1 through 4 carbon atoms substituted by alkoxycarbonyl having 1 through 4 carbon atoms in the alkoxy, carboxy, alkoxycarbonyl having 1 through 4 carbon atoms in the alkoxy, carbamoyl, N-alkylcarbamoyl having 1 through 4 carbon atoms in the alkyl, or $R_1$—CH(OH)— in which $R_1$ represents hydrogen or alkyl of 1 through 3 carbon atoms.

2. A dithiole according to claim 1 wherein Het represents pyrimidin-2-yl, pyrimidin-4-yl, or pyrimidin-5-yl, or pyrimidin-2-yl, pyrimidin-4-yl, or pyrimidin-5-yl substituted by halogen, alkyl of 1 through 4 carbon atoms, alkoxy of 1 through 4 carbon atoms, alkylthio of 1 through 4 carbon atoms, or dialkylamino having 1 through 4 carbon atoms in each alkyl, and R represents alkyl of 1 through 4 carbon atoms, carboxy, alkoxycarbonyl having 1 through 4 carbon atoms in the alkoxy, carbamoyl, or N-alkylcarbamoyl having 1 through 4 carbon atoms in the alkyl.

3. A dithiole derivative according to claim 1 wherein Het represents pyrimidin-2-yl, pyrimidin-4-yl, or pyrimidin-5-yl, or pyrimidin-2-yl, pyrimidin-4-yl or pyrimidin-5-yl substituted by halogen, alkyl of 1 through 4 carbon atoms, alkylthio of 1 through 4 carbon atoms, or dialkylamino having 1 through 4 carbon atoms in each alkyl, and R represents alkyl of 1 through 4 carbon atoms, alkoxycarbonyl having 1 through 4 carbon atoms in the alkoxy, or $R_1$—CH(OH)— in which $R_1$ represents hydrogen or alkyl of 1 through 3 carbon atoms.

4. A 1,2-dithiole according to claim 1 which is 4-ethyl-5-(pyrimidin-5-yl)-1,2-dithiole-3-thione.

5. A 1,2-dithiole according to claim 1 which is 4-methyl-5-(5-methylthiopyrimidin-4-yl)-1,2-dithiole-3-thione.

6. A 1,2-dithiole according to claim 1 which is 5-(5-chloropyrimidin-4-yl)-4-methyl-1,2-dithiole-3-thione.

7. A pharmaceutical anti-bilharzia composition which consists essentially of an effective amount of a 1,2-dithiole as claimed in claim 1 in association with one or more compatible and pharmaceutically acceptable diluents or adjuvants.

* * * * *